United States Patent
Feng

(12) 
(10) Patent No.: US 10,119,893 B2
(45) Date of Patent: Nov. 6, 2018

(54) MECHANICAL PROPERTY TESTER OF BIOLOGICAL SOFT TISSUE

(71) Applicant: SOOCHOW UNIVERSITY, Jiangsu (CN)

(72) Inventor: Yuan Feng, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 318 days.

(21) Appl. No.: 15/106,769

(22) PCT Filed: Jul. 20, 2015

(86) PCT No.: PCT/CN2015/084451
§ 371 (c)(1),
(2) Date: Jun. 20, 2016

(87) PCT Pub. No.: WO2017/008319
PCT Pub. Date: Jan. 19, 2017

(65) Prior Publication Data
US 2017/0199108 A1    Jul. 13, 2017

(30) Foreign Application Priority Data

Jul. 14, 2015 (CN) .......................... 2015 1 0412004

(51) Int. Cl.
*G01N 3/08* (2006.01)
*G01N 33/483* (2006.01)
*G01N 3/04* (2006.01)

(52) U.S. Cl.
CPC ................. *G01N 3/08* (2013.01); *G01N 3/04* (2013.01); *G01N 33/4833* (2013.01); *G01N 2203/0019* (2013.01)

(58) Field of Classification Search
CPC ......... G01N 3/08; G01N 3/12; G01N 33/4833
See application file for complete search history.

(56) References Cited

U.S. PATENT DOCUMENTS 5,616,857 A * 4/1997 Merck, Jr. ................ G01N 3/42
73/82

FOREIGN PATENT DOCUMENTS

| CN | 2102511 U | 4/1992 |
| CN | 101441205 A | 5/2009 |
| CN | 102183622 A | 9/2011 |
| CN | 102967506 A | 3/2013 |
| CN | 104330299 A | 2/2015 |
| FR | 2806804 A | 9/2001 |

* cited by examiner

*Primary Examiner* — Erika J Villaluna
(74) *Attorney, Agent, or Firm* — SZDC Law P.C.

(57) ABSTRACT

A mechanical property tester of biological soft tissue includes a frame body having a workbench, a test head holder disposed on the frame body, a test object fixture base which is disposed on the workbench and located below the test head holder, an acquisition device, and a computer.

9 Claims, 4 Drawing Sheets excess # MECHANICAL PROPERTY TESTER OF BIOLOGICAL SOFT TISSUE

This application is a PCT National Stage Application of PCT/CN2015/084451, filed on Jul. 20, 2015, which claims the benefit of China Patent Application Ser. No. 201510412004.5, field Jul. 14, 2015, which is incorporated by reference for all purposes as if fully set forth herein.

FIELD OF THE INVENTION

The present invention relates to the field of testing equipment's of biological tissues, and more particularly relates to a mechanical property tester of biological soft tissue.

DESCRIPTION OF THE RELATED ART

In the process of research and development of tissue engineering and medical equipment's, the test of mechanical properties of biological tissue is an important step. Biological soft tissues have various mechanical properties due to their own different forms and characteristics. Currently, the test methods of mechanical properties mainly include compression test, tension test and shearing test, and the test instruments usually comprises for example Bose 5500 series, Instron 5900, CSM bioindenter series, TestResource 100 series. However, the existing test instruments have the following disadvantages:

1. Each test instrument only can test particular test object (s), thus, the test object is single, and both the test range and scope are limited.
2. Each test instrument only can test specific function(s), thus, the test function is single.
3. Due to the single test object and test function, multiple test instruments may be needed to perform test on a certain test object, this will lead to high cost.

In view of the above defects, many active researches have been made to develop a novel mechanical property tester of biological soft tissue, so that it is more valuable in industry applications.

SUMMARY OF THE INVENTION

In order to solve the above problems of the prior art, one object of the present invention is to provide a mechanical property tester of biological soft tissue, which can test various test objects, achieve multiple test functions and effectively reduce the test cost.

For the above technical purpose and effects, the invention utilizes the following technical solutions:

a mechanical property tester of biological soft tissue, which comprises a frame body having a workbench, a test head holder disposed on the frame body, a test object fixture base which is disposed on the workbench and located below the test head holder, an acquisition device and a computer, wherein the mechanical property tester of biological soft tissue also comprises:

at least two set of mutually replaceable test heads, one of which is selectively mounted on the test head holder;

at least two set of mutually replaceable fixtures, one of which is selectively mounted on the test object fixture base;

at least two set of mutually replaceable displacement sensors for detecting the movement of the test heads, one set of which is selectively mounted on the frame body; and at least two set of mutually replaceable pressure sensors for detecting the value of pressure on the test object applied by the test heads, one of which is selectively mounted on the test head holder.

The acquisition device is used for collecting the value of pressure detected by the pressure sensor and the mount of movement detected by the movement sensor, and the computer is connected with the acquisition device via signals to analyze the value of pressure and the amount of movement.

Preferably, the fixture selectively mounted on the test object fixture base comprises:

two clamping plates disposed oppositely, each clamping plate comprises a first plate portion and a second plate portion which can be connected as L-shaped, a plurality of grooves are vertically formed on the outer lateral surface of the first plate portion, and a plurality of through-holes are opened on the second plate portion, and a mounting plate for fixing the clamping plates, which is mounted on the test object fixture base.

More preferably, a dovetail groove is opened on the mounting plate, and a dovetail block is projected outwardly from the lateral surface of the second plate portion of the clamping plate for cooperating with the dovetail groove.

Still more preferably, the through-holes are located at two sides of the dovetail block.

Preferably, the test object fixture base comprises:

a bottom base fixed on the workbench;

an X-axis base disposed on the bottom base, which is movable along the front-rear direction of the workbench relative to the bottom base; and a Y-axis base on which the fixture is mounted, the Y-axis base is disposed on the X-axis base and movable along the left-right direction of the workbench relative to the X-axis base.

More preferably, a dovetail block is projected upwardly from the bottom base and the X-axis base respectively, and a dovetail groove is provided on the X-axis base and the Y-axis base respectively, for cooperating with the dovetail grooves on the bottom base and the X-axis base.

Preferably, the test head holder, the pressure sensor and the test head are orderly connected into a line from up to down.

More preferably, the test head is fixed on the test head holder by a sleeve, the sleeve is detachably mounted below the pressure sensor.

Still more preferably, the frame body also comprises:

an elevating device vertically fixed on the workbench, and a fixing plate fixed on the elevating device, and the test head holder is detachably mounted on the fixing plate.

Still other more preferably, the frame body also comprises a sliding rod vertically disposed on the workbench, a displacement sensor mounting base is clamped on the sliding rod, and the displacement sensor is installed on the displacement sensor mounting base, the sliding rod and the elevating device are relatively disposed at two sides of the test object fixture base, and the displacement sensor is movable in up-down direction along the sliding rod.

Due to the above technical solutions, the present invention has the following advantages as compared with the prior art: different kind of test heads, fixtures, displacement sensors and pressure sensors can be selectively mounted as required, and thus the test objects and test functions are various. In the invention the multiple test objects and a plurality of test functions can be achieved by means of one mechanical property tester of biological soft tissue, thus the cost can be greatly reduced and the applicability is very extensive.

The present invention is explained more precisely with reference to the figures attached, by way of example only, in which:

DESCRIPTION OF THE PREFERRED EMBODIMENTS

The invention will be further illustrated in more detail with reference to accompanying drawings. It is noted that, the following embodiments are intended for purposes of illustration only and are not intended to limit the scope of the invention.

Figure 1:
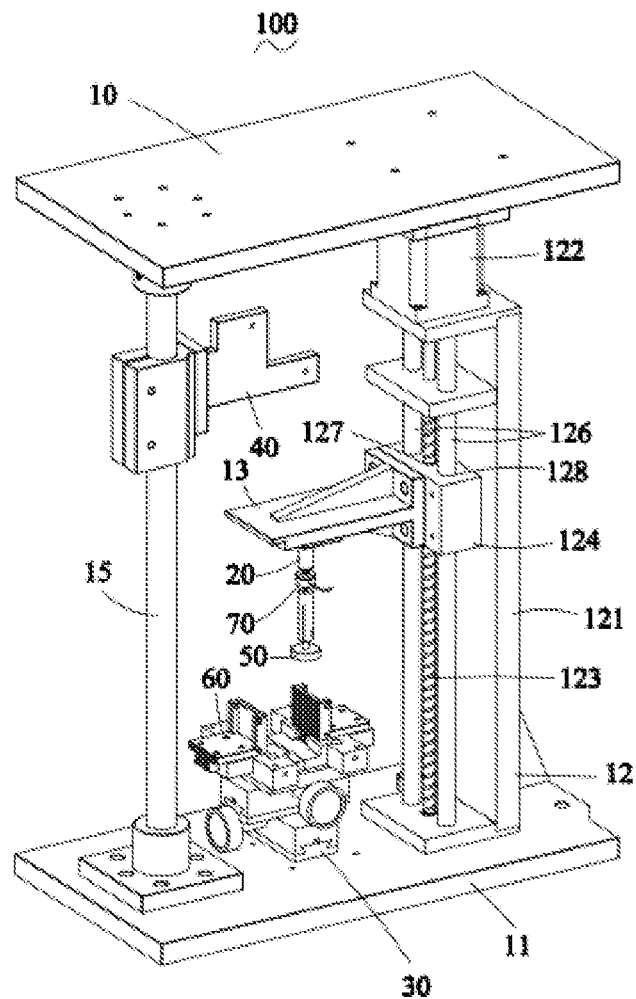
FIG. 1 is a schematic view of a mechanical property tester of biological soft tissue according to the invention.
Figure 2:
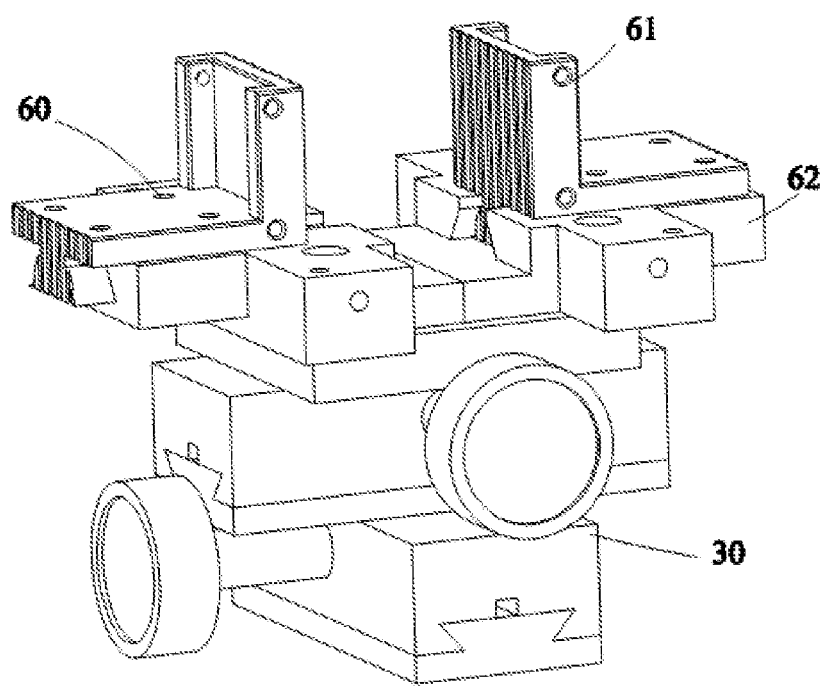
FIG. 2 is a perspective view of the fixture of the FIG. 1.
Figure 3:
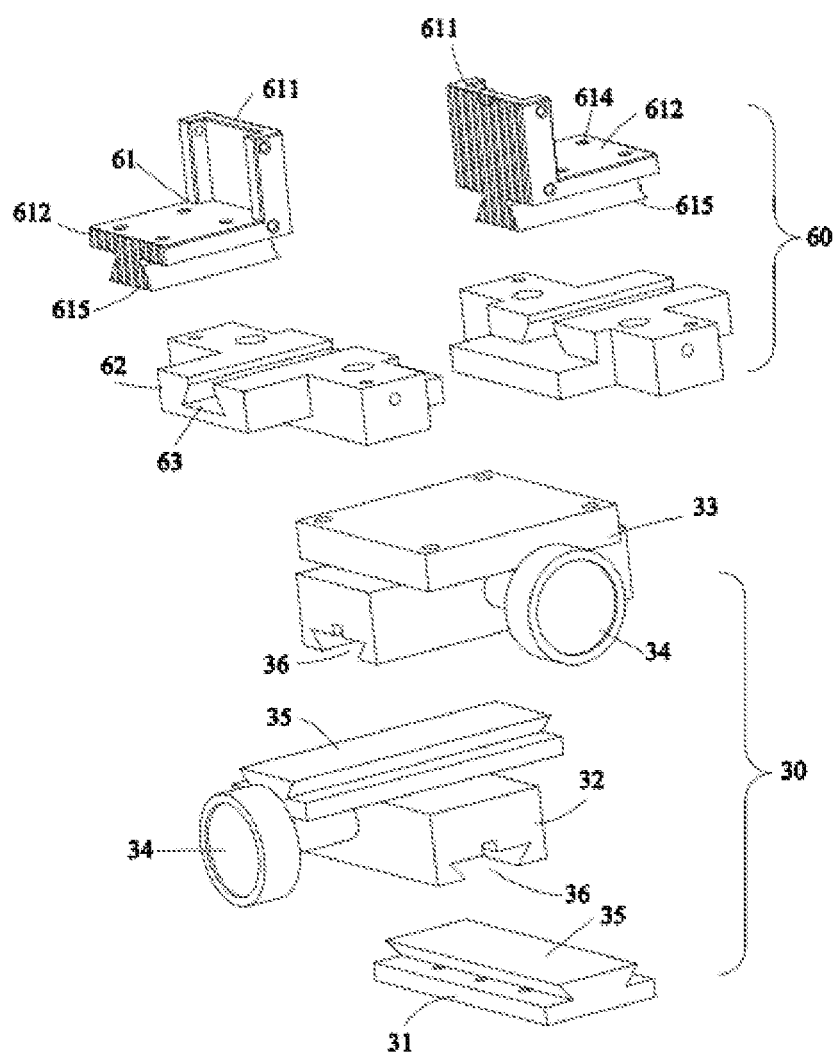
FIG. 3 is an exploded view of the fixture of the FIG. 2.
Figure 4:
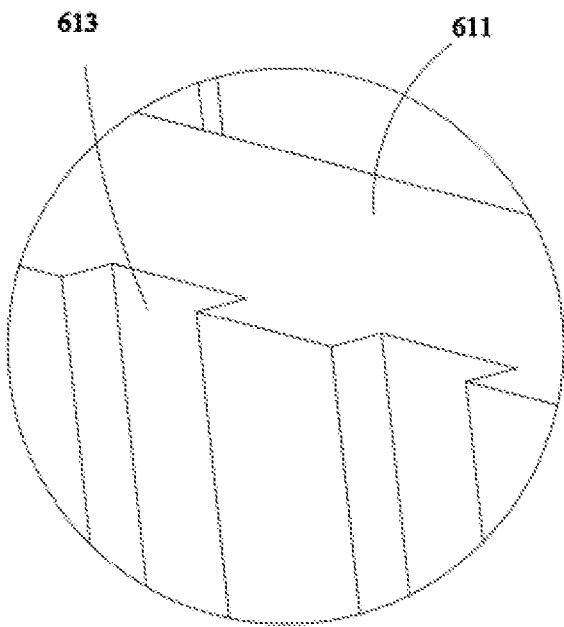
FIG. 4 is an enlarged view of portion A of the FIG. 2.
Figure 5:
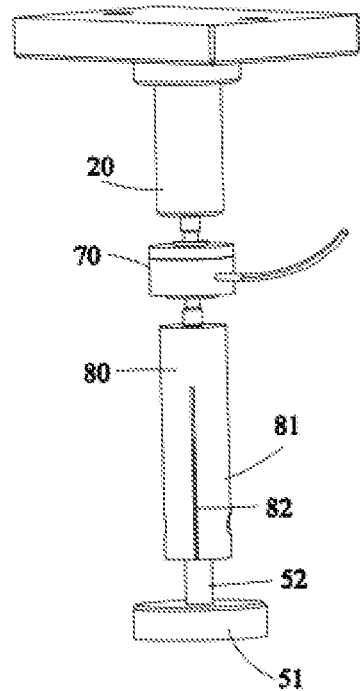
FIG. 5 is a partial schematic view of the FIG. 1.

Referring to FIG. 1 to FIG. 5, a mechanical property tester of biological soft tissue 100 is disclosed in a preferred embodiment of the invention, the mechanical property tester of biological soft tissue 100 is used to test biological soft tissues (hereinafter referred to as "test object(s)" (not shown). The mechanical property tester of biological soft tissue 100 comprises a frame body 10, a test head holder 20 disposed on the frame body 10, a test object fixture base 30, at least two set of mutually replaceable test heads 50 which can test different test objects or characteristics, at least two set of mutually replaceable fixtures 60 for fixing different test objects, at least two set of mutually replaceable displacement sensors (not shown) for testing different range, at least two set of mutually replaceable pressure sensors 70 for testing different ranges of pressure value, an acquisition device (not shown) and a computer (not shown). The frame body 10 comprises a workbench 11, an elevating device 12, a fixing plate 13 fixed on the elevating device 12 and a sliding rod 15 vertically disposed on the workbench 11. The elevating device 12 comprises a base body 121 vertically disposed on the workbench 11, a screw motor 122 disposed on the top of the base body 121, a screw rod 123 arranged within the base body 121 and a moving block 124 disposed on the screw rod 123. The screw rod 123 is electrically connected to the screw motor 122 and the screw rod 123 is controlled by the screw motor 122 to rotate. Polished rods 126 parallel to the screw rod 123 are provided at two sides of the screw rod 123, and a threaded hole 127 is opened on the moving block 124 cooperating with the screw rod 123, and polished rod holes 128 are opened on the moving block 124 at two sides of the threaded hole 127. The polished rods 126 extend through the polished rod holes 128. The fixing plate 13 is fixed on the moving block 124. The sliding rod 15 and the elevating device 12 are oppositely disposed at two sides of the test object fixture base 30, and the displacement sensor is provided on the sliding rod 15. In this embodiment, a displacement sensor mounting base 40 is clamped on the sliding rod 15 and is movable in up-down direction along the sliding rod 15. The displacement sensor is mounted on the displacement sensor mounting base 40. In this embodiment, the displacement sensor is replaced by replacing the displacement sensor mounting base 40.

A test object is fixed by means of a fixture 60, and the test object fixture base 30 is provided on the workbench 11 and located below the test head holder 20. One of the at least two set of fixtures 60 is selectively mounted on the test object fixture base 30. In this embodiment, the fixture 60 selectively mounted on the test object fixture base 30 comprises two clamping plates 61 opposite to each other and mounting plates 62 for fixing the clamping plates 61. There are two mounting plates 62 which are used for fixing one clamping plate respectively. Each mounting plate 62 is mounted on the test object fixture base 30 by a fastener (not shown). A first dovetail groove 63 is opened on each mounting plate 62. Each clamping plate 61 comprises a first plate portion 611 and a second plate portion 612 which are connected as L-shaped. Several grooves 613 are vertically provided on the outer lateral surface of the first plate portion 611, and several through-holes 614 are opened on the second plate portion 612. A first dovetail block 615 is projected outwardly from the lateral surface of the second plate portion 612 of the clamping plate 61, and the through-holes 614 are located at two sides of the first dovetail block 615, and the first dovetail groove 63 is cooperated with the first dovetail block 615. The clamping plate 61 is fixed on the mounting plate 62 by a bolt. In this embodiment, the fixture 60 can fix two different test objects. When the grooves 613 of the first plate portion 611 of one clamping plate 61 and the grooves 613 of the first plate portion 611 of another clamping plate 61 are disposed face to each other, the fixture 60 can clamp a block test object. When the grooves 613 of the first plate portion 611 of one clamping plate 61 and the grooves 613 of the first plate portion 611 of another clamping plate 61 are disposed far away from each other, the fixture 60 can clamp a strip or film test object.

The test object fixture base 30 includes a bottom base 31 fixed on the workbench 11, a X-axis base 32 disposed on the bottom base 31 and a Y-axis base 33 disposed on the X-axis base 32. The X-axis base 32 is movable in front-rear direction along the workbench 11 relative to the base 31. The Y-axis base 33 is movable in left-right direction along the workbench 11 relative to the X-axis base 32. The fixture 60 is mounted on the Y-axis base 33. The X-axis base 32 and the Y-axis base 33 respectively are provided with a handle 34 thereon, so that they can be moved easily. A second dovetail block 35 is projected upwardly from the bottom base 31 and the X-axis base 32 respectively. Second dovetail grooves 36 are provided on the X-axis base 32 and the Y-axis base 33 respectively for cooperating with the second dovetail blocks 35 on the bottom base 31 and X-axis base 32.

One of the at least two set of test heads 50 is selectively mounted on the test head holder 20. One of the at least two set of pressure sensors 70 is selectively mounted on the test head holder 20, and the pressure sensor 70 is used for detecting the value of pressure on the test object applied by the test head 50. One of the at least two set of displacement sensors is selectively mounted on the displacement sensor mounting base 40, and the displacement sensor detects the amount of movement of the test head 50. The test head 50, the pressure sensor 70 and the displacement sensor are appropriately selected according to the test objects to be tested and/or test functions. The test head holder 20, the pressure sensor 70 and the test head 50 are orderly connected into a line from up to down. In this embodiment, the test head 50 is fixed on the test head holder 20 by a sleeve 80, and the sleeve 80 is detachably mounted below the pressure sensor 70. The sleeve 80 has a mounting chamber (not shown) and a wall body forming the mounting chamber, a narrow gap is opened on the wall body 81 which is cylindrical. When the test head is a surgical blade, the narrow gap 82 fixes the surgical blade, and the width of the narrow gap 82 is designed in terms of the width of the surgical blade. The test head 50 is a cylindrical pressure head. Certainly, the pressure head can be configured as other pressure heads with particular geometry in terms of the mechanical properties of the test object. In this embodiment, the pressure head 50 has a pressure head portion 51 and a rod body 52 extended from the pressure head 51, the rod body 52 extends into the mounting chamber and fixed by a fastener (not shown). In this embodiment, parts of the fixture 60 are connected as follows: the test head holder 20 is connected with the pressure sensor 70 by a thread, the pressure sensor 70 is connected with the sleeve 80 by means of a thread, and the sleeve 80 is connected with the pressure head 50 by means of insertion. The test head holder 20 is detachably mounted on the fixing plate 13. Certainly, in other embodiments, the test head 50 can be selected as other type of test heads according to the functions being tested and/or the kinds of the test objects. For example, when puncture test is to be performed, the test head 50 can utilize a puncture needle. When the damage characteristic of a material is tested, the test head 50 can be used as a surgical blade.

The acquisition device collects the value of pressure detected by the pressure sensor 70, and the amount of movement detected by the displacement sensor. The computer is connected with the acquisition device via signals, and the computer receives the collected detection data from the acquisition device and analyzes the detection data.

The working principle of compression test of the mechanical property tester of biological soft tissue of this embodiment is as follows: firstly, the clamping plate 61 is mounted in terms of the test object to be tested, and the test object is mounted on the fixture 60; the pressure head 50, the pressure sensor 70 and the displacement sensor are selected and mounted in terms of the test object as follows: the displacement sensor is mounted on the displacement sensor mounting base 40, the pressure sensor 70 is mounted on the test object fixture base 30, the sleeve 80 is mounted on the pressure sensor 70 and the pressure head 50 is mounted on the sleeve 80; then, the handle 34 is pulled to adjust the position of the test object as required; finally, the screw motor 122 is activated so that the pressure head 50 is moved down slowly to perform pressure test on the test object, now, the pressure sensor 70 detects the value of pressure on the test object applied by the pressure head 50, the displacement sensor detects the displacement of the pressure head 50, the acquisition device collects the detection data of the displacement sensor and the pressure sensor 70, and the computer receives the collected detection data from the acquisition device and analyzes the detection data. When the tensile test or shearing test is to be taken by the mechanical property tester of biological soft tissue 100, it is only needed to change the test head 50. While other test objects are detected by the mechanical property tester of biological soft tissue 100 or the detection range is changed, it is only needed that one or more of the corresponding fixture 60, the test head, the pressure sensor 70 and the displacement sensor is changed according to the test objects, thus, in the invention the test objects are diversified and a plurality of test functions are achieved, this will facilitate to reduce the cost.

In conclusion, by means of the mechanical property tester of biological soft tissue 100 of the invention, different types of test heads 50, fixtures 60, displacement sensors and pressure sensors 70 can be selectively mounted as required, this will reach various test objects and multiple test functions. Furthermore, because multiple test objects and a plurality of test functions can be achieved by one mechanical property tester of biological soft tissue 100, thus, the cost is greatly reduced and applicability is very extensive.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A mechanical property tester of biological soft tissue, comprising a frame body having a workbench, a test head holder disposed on the frame body, a test object fixture base which is disposed on the workbench and located below the test head holder, and a computer,
    wherein the mechanical property tester of biological soft tissue also comprises:
        a replaceable test head mounted on the test head holder;
        a replaceable fixture mounted on the test object fixture base;
        a replaceable displacement sensor mounted on the frame body for detecting the movement of the test head; and
        a replaceable pressure sensor mounted on the test head holder for detecting the value of the pressure on a test object applied by the test head;
    wherein the computer is connected via signals to analyze the value of pressure and the amount of movement; and
    wherein the replaceable fixture comprises:
        two clamping plates disposed oppositely, each clamping plate comprising a first plate portion and a second plate portion which can be connected in an L-shape, a plurality of grooves being vertically formed on the outer lateral surface of the first plate portion, and a plurality of through-holes being opened on the second plate portion, and
        a mounting plate for fixing the clamping plates, which is mounted on the test object fixture base.

2. The mechanical property tester of biological soft tissue as claimed in claim 1, wherein a dovetail groove is opened on the mounting plate, and a dovetail block is projected outwardly from the lateral surface of the second plate portion of the clamping plate for cooperating with the dovetail groove.

3. The mechanical property tester of biological soft tissue as claimed in claim 2, wherein the through-holes are located at two sides of the dovetail block.

4. The mechanical property tester of biological soft tissue as claimed in claim 2, wherein the test object fixture base comprises:
    a bottom base fixed on the workbench;
    an X-axis base disposed on the bottom base, which is movable along the front-rear direction of the workbench relative to the bottom base; and
    a Y-axis base on which the fixture is mounted, the Y-axis base being disposed on the X-axis base and movable along the left-right direction of the workbench relative to the X-axis base.

5. The mechanical property tester of biological soft tissue as claimed in claim 4, wherein a dovetail block is projected upwardly from the bottom base and the X-axis base respectively, and a dovetail groove is provided on the X-axis base and the Y-axis base respectively, for cooperating with the dovetail block on the bottom base and the X-axis base.

6. The mechanical property tester of biological soft tissue as claimed in claim 1, wherein the test head holder, the pressure sensor and the test head are orderly connected into a line from up to down.

7. The mechanical property tester of biological soft tissue as claimed in claim 6, wherein the test head is fixed on the test head holder by a sleeve, the sleeve being detachably mounted below the pressure sensor.

8. The mechanical property tester of biological soft tissue as claimed in claim 6, wherein the frame body also comprises:
- an elevating device vertically fixed on the workbench, and
- a fixing plate fixed on the elevating device, the test head holder being detachably mounted on the fixing plate.

9. The mechanical property tester of biological soft tissue as claimed in claim 8, wherein the frame body also comprises a sliding rod vertically disposed on the workbench, a displacement sensor mounting base being clamped on the sliding rod, and the displacement sensor being installed on the displacement sensor mounting base, the sliding rod and the elevating device being relatively disposed at two sides of the test object fixture base, and the displacement sensor being movable in up-down direction along the sliding rod.

* * * * *